(12) United States Patent
Elsheikh et al.

(10) Patent No.: US 7,485,598 B2
(45) Date of Patent: Feb. 3, 2009

(54) HIGH PRESSURE CATALYST ACTIVATION METHOD AND CATALYST PRODUCED THEREBY

(75) Inventors: Maher Y. Elsheikh, Wayne, PA (US); Beatrice Boussand, Sainte Foy les Lyon (FR)

(73) Assignee: Arkema Inc., Philadelphia, PA (US)

( * ) Notice: Subject to any disclaimer, the term of this patent is extended or adjusted under 35 U.S.C. 154(b) by 305 days.

(21) Appl. No.: 11/472,008

(22) Filed: Jun. 21, 2006

(65) Prior Publication Data

US 2007/0299286 A1 Dec. 27, 2007

(51) Int. Cl.
*B01J 27/12* (2006.01)

(52) U.S. Cl. ............... 502/224; 502/226; 502/228; 502/229; 502/231

(58) Field of Classification Search ............... 502/224, 502/226, 228, 229, 231
See application file for complete search history.

(56) References Cited

U.S. PATENT DOCUMENTS

| 5,155,082 | A |   | 10/1992 | Tung et al. |
| 5,494,876 | A | * | 2/1996  | Tsuji et al. ............... 502/224 |
| 5,744,658 | A |   | 4/1998  | Scott et al. |
| 5,981,813 | A |   | 11/1999 | Cuzzato et al. |
| 6,187,280 | B1 |  | 2/2001  | Cuzzato et al. |
| 6,403,524 | B2 |  | 6/2002  | Scott et al. |
| 6,755,942 | B1 |  | 6/2004  | Baker et al. |
| 6,780,815 | B2 |  | 8/2004  | Cerri et al. |
| 6,858,762 | B2 |  | 2/2005  | Baker et al. |
| 2003/0022785 | A1 | | 1/2003 | Cerri et al. |
| 2004/0102664 | A1 | | 5/2004 | Iikubo et al. |
| 2005/0020862 | A1 | | 1/2005 | Tung et al. |
| 2005/0070746 | A1 | | 3/2005 | Tung et al. |
| 2005/0080302 | A1 | | 4/2005 | Baker et al. |
| 2005/0090698 | A1 | | 4/2005 | Merkel et al. |

FOREIGN PATENT DOCUMENTS

WO   WO 2005/012213 A1   2/2005

* cited by examiner

*Primary Examiner*—Elizabeth D Wood
(74) *Attorney, Agent, or Firm*—Steven D. Boyd

(57) ABSTRACT

A process for the activation of a fluorination catalyst in which a catalyst precursor compound, supported or unsupported is first dried and thereafter activated by exposure to an activating agent at a pressure greater that about 100 psig and a temperature grater than about 100° C. The process is particularly suited to the activation of chromium (III) compounds, such as $Cr_2O_3$. The resulted dry, high-pressure activated catalyst was found to provide increase fluorination conversion, with higher selectivity of the desired product.

12 Claims, No Drawings

HIGH PRESSURE CATALYST ACTIVATION METHOD AND CATALYST PRODUCED THEREBY

FIELD OF THE INVENTION

The present invention relates generally to fluorination catalysts. More particularly, the present invention provides a high pressure activation process for preparing fluorination catalysts for use in the fluorination of chlorocarbon, hydrochlorocarbon, hydrochlofluoroalkane and/or chloroalkane compounds and the catalyst activated via the process.

BACKGROUND OF THE INVENTION

There are numerous processes directed to the manufacture of fluorinated organic compounds. Many of these processes involve the reaction of an organic starting material, such as chloroalkane and/or a chloroalkene, with hydrogen fluoride ("HF") in the presence of a fluorination catalyst to produce the desired fluorinated compound or compounds. The product stream from this type of reaction typically includes, in addition to the fluorinated organic compound or compounds, unreacted chloroalkane and/or chloroalkene starting materials and unreacted HF. It is common in such processes to separate the unreacted starting materials from the product stream and to recycle those components to the reaction step. U.S. Pat. No. 6,780,815 discloses a process for preparing a fluorination catalyst using a low pressure activating step followed by a high pressure activating step. U.S. Pat. No. 6,187,280 discloses a process for preparing aluminum fluoride having an essentially gamma crystalline structure and a surface area of at least 150 m$^2$/g and pore volume not lower than 0.3 cm$^3$/g by fluorinating alumina with gaseous HF at a temperature higher than 300° to 400° C. wherein the gaseous HF is diluted with an inert gas and has a partial pressure of between 0.1 and 0.5 and where the alumina has a surface area of at least 150 m$^2$/g and from 0.5 to 15% by weight of silicon oxide. International Patent Application number PCT/EP2004/051624 discloses a process for activation of AlF$_3$ based catalyst by treating crude AlF$_3$ for more than 5 hours with a gas stream at a temperature from 300° to 450° C. US application No. 2005/0080302 discloses a process for the manufacture of halocarbons with HF using a Cr$_2$O$_3$ catalyst prepared by pyrolysis of (NH$_4$)$_2$Cr$_2$O$_7$ to produce Cr$_2$O$_3$ and pretreating with HF. The temperature of the reaction can be from 200° C. to 400° C. and the pressure is not critical and is selected so that the reaction starting materials and products are maintained in the vapor state at the operating temperature.

The present inventor recognized a need in the art for an improved fluorination catalyst and a process for the preparation of fluorination catalyst which will result in improved conversion, selectivity and/or yield of fluorinated organic compounds and increased catalyst life.

SUMMARY OF THE INVENTION

The present inventor has discovered a high pressure catalyst activation method that produces fluorination catalyst which provide enhanced yield when fluorinating organic compounds and enhanced longevity of the catalyst.

Applicant has discovered a process for activating a fluorination catalyst precursor, which comprises drying the catalyst precursor and thereafter exposing the dried catalyst precursor to an activating agent under high pressure conditions. Activation of the catalyst precursor with an activating agent at higher pressures produces a catalytically active compound which exhibits enhance activity and catalyst life.

As used herein, the term "catalytically active compound" is intended to refer to compounds that catalyze fluorination of organic compounds and to compounds that can be converted, by the present process, to such compounds. It is to be understood that this term encompasses not only fresh, unused catalytically active compounds but also compounds that have been previously used as a fluorination catalyst and subsequently can be regenerated and/or reactivated by the present process.

As used herein, the term "substantial thermal stability" is intended to refer to conditions in which the rate of change of temperature has slowed to a substantial extent, and preferably is substantially constant for a measurable period of time, under adiabatic conditions. In other words, a catalyst has reached "substantial thermal stability" when the rate of heat generation during the conditioning step is substantially reduced, and preferably is substantially zero. As explained in more detail hereinafter, the preferred activating step of the present invention result in an exothermic reaction involving the catalyst, and "substantial thermal stability" is achieved when such exotherm is substantially dissipated.

According to one preferred embodiment, the high pressure activating step comprises exposing a catalyst precursor compound to an activating agent composition that comprises an activating compound and an inert carrier at high pressure, preferably the concentration of the activating compound in the activating agent composition increases during at least a portion of the activating step.

For example, the activating step in certain preferred embodiments comprises first drying the catalyst precursor and thereafter exposing the dried catalyst precursor to an activating agent composition at a high pressure. Applicants have found that activating the catalyst precursor using such a high pressure technique is highly effective in producing a catalyst that tends to exhibit a high conversion in fluorination reactions and an extend catalyst life.

DETAILED DESCRIPTION OF THE INVENTION

The present invention relates to the activation of a fluorination catalyst precursor by exposing catalyst precursor compound(s) to drying and thereafter an activating agent composition at high pressures. The term "untreated catalyst precursor compounds" is used herein in its broad sense to designate a precursor of a catalytically active compound, which will be subjected to the process steps of the present invention. Thus, the term "untreated catalyst precursor compounds" is intended to include within its meaning not only fresh, untreated catalyst precursor compounds, but also to such compounds which have previously been treated by the present invention and/or by other treatment operations and are to be regenerated and/or reactivated.

A large number of potentially catalytically active precursor compounds are known, and it is contemplated that all such compounds can be treated in accordance with the processes of the present invention to produce fluorination catalyst. According to preferred embodiments, fluorination catalysts prepared in accordance with the present invention are compounds that are catalytically active in the reaction of hydrogen fluoride (HF) with halogenated hydrocarbons, preferably chlorinated hydrocarbons (CHCs) such as chloroalkanes and chloroalkenes. Fluorination catalysts prepared in accordance with the present invention are suitable for the fluorination of chloroalkanes and/or chloroalkenes to hydrochlorofluorocarbons (HCFCs) and/or hydrofluorocarbons (HFCs). Fluorination catalysts prepared in accordance with the present invention are also suitable for the fluorination of HCFCs to HFCs. The present method finds particularly advantageous utility in the preparation of catalysts for the fluorination of chlorinated olefins, and particularly perchlorinated olefins, such as perchloroethylene (PCE) or trichloroethylene (TCE) to hyrofluorcarbons (HFCs) such as pentafluoroethane (HFC-125) or tetrafluoroethane (HFC-134a).

Suitable catalyst precursor compounds of the present invention are well known in the art and include various inorganic compounds. For example oxides, halides, nitrates, sulfates and the like of metals such as aluminum, cobalt, manganese, iron, zinc, chromium or mixtures thereof. The present invention is particularly well suited for the preparation of chromium-based catalysts.

Chromium based fluorination catalysts are typically and preferably based more specifically upon chromia. The chromia may be, for example, fluorinated so that the fluorination catalyst is a chromium oxyfluoride species. Furthermore the chromia may comprise activity promoting amounts of other metals, for example zinc, nickel, cobalt, manganese, magnesium or mixtures thereof. The chromia-based catalyst may be supported on a support system. The support system may be, for example a metal oxide such as alumina ($Al_2O_3$), magnesia (MgO), a metal fluoride, for example aluminum fluoride and magnesium fluoride or the support system may be an activated carbon, or HF activated carbon.

The present methods can be carried out in a wide variety of environments and in batch, continuous, and/or semi-continuous operations. It is generally preferred, however, that the methods are carried out in continuous or semi-continuous operations.

The catalyst precursor compounds to be processed in accordance with the present invention can be provided substantially free of water or preferably they are subjected to a drying step, which preferably produces a compound substantially free of unbound water. The drying step preferably comprises passing a drying gas, preferably nitrogen, over and in intimate contact with the untreated catalyst precursor so as to carry away a substantial portion of any unbound water present in, on or otherwise associated with the untreated catalyst. The drying step can be carried out at a pressure of from atmospheric up to 300 psig. The temperature of the catalyst precursor compound during the drying step can range from room temperature up to about 400° C., preferably from about 100° to about 200° C. at a contact time of from about 1 to 100 seconds, preferably from about 10 to 40 seconds, for approximately 1-50 hours, preferably between 5-20 hours. An in-line moisture analyzer can be used to monitor the water content of the effluent stream.

Any heating means known in the art may be used to heat the catalyst precursor compound to the indicated ranges. For example, the catalyst precursor compound may be heated directly by heating the drying gas or indirectly by heating the vessel containing the catalyst precursor compound.

The present method includes exposing the dried precursor compound, to an activating agent in a single high pressure-activating step. The single high pressure activating step is carried out at a pressure of above about 100 psig, preferably from about 200 psig to about 400 psig. The temperature of the single high pressure activation step can range from about 100° to about 400° C., preferably between about 200° and about 300° C.

The activating agent is preferably HF. The HF can be fed to the system as a gas or a liquid and is preferably fed with an inert carrier gas such as nitrogen. The proportion of HF to nitrogen can range from about 1-20 mole % HF in nitrogen.

The preferred single step high pressure activation with HF results in fluorination of the catalyst precursor compound which results in the generation of water and of heat. The single high pressure activation step preferably includes removing from the catalyst both the heat and the water generated during the single high pressure activation step. Other activating agents such as hydrochlorofluorocarbons; for example $CF_3CH_2Cl$ (HCFC-133a), $CHClF_2$ (HCFC-22), $CF_3CHCl_2$ (HCFC-123), $CH_2ClF$ (HCFC-31), and/or hydrofluorocarbons; for example $CF_3CH_2F$ (HFC-134a), $CF_3CH_3$ (HFC-143a) and $CF_2H_2$ (HFC-32) and the like can be used as activators. Unlike HF, when HCFCs or HFCs are used as activating agents, water is not formed or diluted water with other coproduct such as $CO_2$ and/or CO is formed. The use of an activating agent other than HF can result in less corrosion to the equipment. Also, an activation process using an activating agent other than HF can be carried out as an in-situ activation.

Numerous heat and water removal techniques can be used in accordance with the present invention, and all such steps are encompassed within the scope hereof. With respect to the water removal step, it is preferred that the water is removed as a feature of the activation step. For example, it is preferred that the high pressure activating gas is maintained in intimate contact with the catalyst for a time sufficient to not only activate the catalyst but also to allow a substantial portion of the generated water to be desorbed by, entrained in, or otherwise carried away by the activating gas. Removal of the activating gas from the catalyst also then results in removal of water from the catalyst. Similarly, the heat can be removed from the catalyst by allowing the activating gas to work as a heat absorber. In addition, other techniques can be used to remove the heat of the exothermic reaction from the catalyst, such as external cooling of the vessel containing the catalyst.

It is also generally preferred that the high pressure activating step is conducted as a continuous process in which the activating gas is passed over and in intimate contact with the catalyst and then removed from the catalyst by passing the gas through the vessel containing the catalyst. In such embodiments, the residence time that the high pressure activating gas is in contact with the catalyst can vary widely depending on numerous factors associated each individual application, such as the type and amount of the catalyst, the type and amount of activating gas, and like factors. In general, the contact time of the HF and nitrogen can vary between 10 and 100 seconds. The high pressure activation is continued until water evolution ceases and the exotherm is dissipate, i.e. steady state conditions. The process can take up to 30 hours. The HF contact time is the time that the HF gas is physically in contact with the catalyst bed, and is sometime called to residence time. The total catalyst volume/total gas flow, adjusted to the operating temperature and pressure measures contact time. The process time is how long the HF gas, and any other gases have been continuously feed to the reactor at the operating conditions.

The dry activated catalyst can be used for the fluorination of HCFCs such as 133a, 123 and 31 etc; to the corresponding HFC, 134a, 125 and 32 respectively. The catalyst can also be used for the gas phase fluorination of chloroalkenes such as vinyl chloride to 152a, vinylidene chloride to 141b, 142b and 143a, trichloroethylene to 133a/134a and/or perchloroethylene to $CF_3CHCl_2$ (HCFC 123), $CF_3CHClF$ (HCFC 124) and $CF_3CHF_2$ (HFC 125). The fluorination process can be carried out at temperature ranging form about 100° to 400° C. and preferably between about 200° to 300° C. The operating pressure can be varied between atmospheric pressure and 400 psig and is preferably between about 100 to 300 psig. The contact time is not critical and can range from about 4 to 20 seconds. The molar ratio of HF to organic being fluorinated ranges from about 1/1 to 10/1. The most preferred ratio ranges from about 2/1 to 5/1 of HF/organic. To maintain the catalyst lifetime for extended periods of time, it is recommended to maintain low levels of oxygen in the form of air as a co-feed together with the organic. The amount of oxygen can range from about 0.1 to 2% of the organic co-feed preferably from about 0.1 to 1%. In some processes, where food grade HCl is recovered as a co-product, it is desirable to co-feed zero air or a minimum amount of air. Processes known in the art such as distillation, extractive distillations and/or adsorption using a solid adsorbent can recover the HCl co-product.

The present invention is illustrated in more detail in the following non-limiting examples.

EXAMPLE 1

Atmospheric Pressure $Cr_2O_3$ Catalyst Activation

Twenty cc's (27.6 grams) of a commercially available chromium oxide ($Cr_2O_3$) catalyst (E-410 available from Engelhard) in the form of 1/8"×1/8" cylinders was loaded into a 1"×12", vertical fixed bed reactor made out of Hastelloy C. The reactor was heated using a three-zone electric tube furnace. The reactor inlet fittings included fittings for HF gas, organic feed, air and nitrogen. Liquid HF feed was measured and controlled using a liquid mass flow meter controller. The liquid HF was vaporized using a pre-heater prior to feeding to the reactor. The organic (HCFC-133a) was fed using a high pressure ISCO pump. Nitrogen and air feed were controlled and measured using gas mass flow meter controllers. The catalyst bed was first dried by heating to 150° C. in the presence of a nitrogen feed flowing at 50 ccm, for 18 hours. Subsequently a mixture of HF and nitrogen was fed to the dried catalyst bed at atmospheric pressure. The ratio of HF to nitrogen was varied and the operating temperature was increased over time as shown in Table 1

TABLE 1

Chromium Oxide (Engelhard E-410) Catalyst Activation

| Time (hours) | Feed rate HF (g/hr/$N_2$cc/m) | Temp (° C.) |
|---|---|---|
| 0-2 | 8/400 | 100 |
| 2-4 | 8/300 | 150 |
| 4-6 | 8/200 | 250 |
| 6-8 | 8/100 | 350 |
| 8-18 hours | Pure HF 8 g/hr | 350 |

After activating the catalyst for 18 hours. The physically adsorbed HF was desorbed at 350° C., using nitrogen flow at 100 ccm for 18 hours. The dry activated catalyst was unloaded and analyzed for the fluorine content, surface area (SA), pore volume (PV) and $Cr^{+6}$ content. Table 2 summarizes the analytical results.

TABLE 2

Analysis of atmospheric pressure activated catalyst

| Fluorine | 16.80% |
|---|---|
| SA | 85.00 $m^2$/g |
| PV | 00.19 $m^3$/g |
| $Cr^{+6}$ | 03.27% |

Thirteen cc's of the activated catalyst was reloaded into the reactor and subjected to additional fluorination at the operating pressure 162 psi at 350° C. using HF feed at 8 g/hr together with nitrogen co-feed at 100 ccm for ½ hr. When the exotherm resulting from the reaction dissipated a process feed comprising 12 g/hr of HF, air at 2.5 ccm, organic (HCFC-133a) at 0.45 ccm (90.98% pure) began. These feed conditions correspond to 2/1 molar ratio of HF/HCFC-133a, $O_2$ 0.5% based upon HCFC-133a and a contact time of 12 seconds. The organic product obtained from the reactor together with HCl co-product and excess HF was scrubbed using 17% KOH solution, dried with anhydrous $CaSO_4$ and analyzed using Gas Chromatograph. Conversion of HCFC-133a to HFC-134 was 10% and selectivity for HCFC-134a was 93.7%, as shown in Table 3. Numbers are reported in moles percent.

TABLE 3

| Fluorination of 133a | | | | | | | | |
|---|---|---|---|---|---|---|---|---|
| %133aConv. | %134a | %134 | %23/32 | %110 | %120 | %1122 | % CO | % $CO_2$ |
| 10 | 93.7 | 1 | .5 | .3 | 2.3 | 0 | .9 | 1 |

EXAMPLES 2-4

Evaluation of High Pressure Activated $Cr_2O_3$ Catalyst

A high pressure catalyst activation process in accordance with the present invention was carried out as follows. The reactor was loaded with 12.38 kg of chromium oxide catalyst precursor. The catalyst precursor was dried at 350° C. using a nitrogen flow of 1 liter/minute at atmospheric pressure for 18 hours. The dried catalyst was thereafter pressurized to 235 psig using nitrogen and the temperature raised to 350° C. Thereafter, a mixture of HF at 3 g/m and nitrogen at 7 liters/minute was fed over the catalyst bed in such away that the temperature resulting from the reaction exotherm did not exceed 370° C. After the exotherm dissipated, pure HF at 3 g/minute was fed over the catalyst bed for 18 hours. The activated catalyst was analyzed. The chemical and physical properties of the activated catalyst are summarized in Table 4.

TABLE 4

Physical and Chemical Properties of High Pressure Activated Catalyst

| F content | 22.20% |
|---|---|
| SA | 43.90 $m^2$/g |
| PV | 00.19 $m^3$/g |
| CS | 23.30 lb |
| $Cr^{+6}$ | 201.00 ppm |
| Attrition | 03.90% |

Thirteen cc's of the high-pressure activated catalyst was loaded into the vertical reactor described in Example 1. A mixture of HF and nitrogen was fed over the catalyst bed at the pressures and feed rates shown in Table 5, no exotherm was observed.

TABLE 5

Prefluorination for the preactivated Engelhard catalyst

| Time | T C | P psi | Nitrogen ccm | HF g/hr. | Air ccm | Observation |
|---|---|---|---|---|---|---|
| 1:30 | 200 | 162 | 100 | 5 | 0 | No exotherm |
| 1:40 | 250 | 162 | 100 | 5 | 0 | No exotherm |
| 2 | 300 | 162 | 100 | 5 | 0 | No exotherm |
| 2:30 | 350 | 162 | 100 | 5 | 0 | No exotherm |
| 2:50 | 350 | 162 | 80 | 5 | 0 | No exotherm |
| 3 | 350 | 162 | 60 | 5 | 0 | No exotherm |
| 3:10 | 350 | 162 | 40 | 5 | 0 | No exotherm |
| 3:15 | 350 | 162 | 0 | 5 | 2.5 | No exotherm |
| 3:35 | 350 | 162 | 82 bottom | 12 | 2.5 | No exotherm |

The catalyst was evaluated using the same feed conditions as Example 1 (HCFC-133a at 0.45 ccm, HF at 12 g/hr, air at 2.5 ccm) at a temperature of 350° C. and a pressure of 162 psi. These feed conditions correspond to 2/1 molar ratio of HF to HCFC-133a, $O_2$ to organic ratio of 0.5% and a contact time 12 seconds. Conversion of the HCFC-133a obtained was nearly 18% and selectivity of 134a was approximately 99%.

The contact time was than lowered to 7.8 seconds, Example 3. The conversion remained very high at 18% and the selectivity for HCFC-34a was near 99%. When contact time was further lowered to 5.6 seconds. Then, conversion decreased to 11.3% and selectivity for HCFC-134a dropped to 96.6%, Example 4. These results are summarized in Table 6.

TABLE 6

Performance of High Pressure (235 psig) Activated $Cr_2O_3$ Catalyst

|  | Example 2 | Example 3 | Example 4 |
|---|---|---|---|
| Temp ° C. | 350 | 350 | 350 |
| Pressure PSI | 162 PSI | 162 | 162 |
| Molar ratio HF/133a | 2/1 | 2/1 | 2/1 |
| Contact Time seconds | 12 | 7.8 | 5.6 |
| O2 %133a | .5 | .5 | .5 |
| % Conversion | 18 | 18 | 11.3 |
| % Selectivity | 99 | 99 | 96.6 |

Table 7 summarizes the effect of activation pressure on the performance of the resulting catalyst evaluated under the same operating conditions of: temperature 350° C., Molar ratio HF to HFC-133a 2 to 1, contact time 12 seconds, $O_2$ 0.5% from HCFC-133a.

TABLE 7

Comparison between high pressure activated unsupported chromium oxide catalyst and low pressure activated catalyst for the fluorination of 133a to 134a

| Activating pressure psig | %134a yield[1] |
|---|---|
| 14.7 | 9.37 |
| 235 | 17.82 |

[1]Yield % conversion x % selectivity (mole percent)

While the present invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

What is claimed is:

1. A process for high pressure activation of a fluorination catalyst, comprising the steps of:
    drying a catalyst precursor compound by exposure to a combination of heat and an inert gas flow to form a dry catalyst precursor compound; and
    exposing said dry catalyst precursor compound, in a single catalyst activation step, to an activating agent at a pressure greater than about 100 psig, at a temperature above about 100° C. for a period of time sufficient to achieve steady state conditions.

2. The process of claim 1 wherein said catalyst precursor compound is selected from the group consisting of oxides, halides, nitrates and sulfates of metals selected from aluminum, cobalt, manganese, iron, zinc, chromium or mixtures thereof.

3. The process of claim 2 wherein said catalyst precursor is supported.

4. The process of claim 2 wherein said catalyst precursor is unsupported.

5. The process of claim 2 wherein said catalyst precursor compound further includes an activity promoter selected from the group consisting of zinc, nickel, cobalt, manganese, magnesium and mixtures thereof.

6. The process of claim 1 wherein said drying takes place at a pressure of from atmospheric up to 400 psig.

7. The process of claim 1 wherein said drying takes place at a temperature of from room temperature to about 400° C.

8. The process of claim 1 wherein said activation step takes place at a pressure of from about 200 to about 400 psig.

9. The process of claim 1 wherein said activating agent is hydrogen fluoride.

10. The process of claim 9 wherein said activating agent further comprises an inert carrier gas.

11. The process of claim 10 wherein said inert cater gas is selected from the group consisting of nitrogen, helium, argon and mixtures thereof.

12. The process of claim 11 wherein the ratio of activating agent to cater gas ranges form about 1 to 20 mole % activating agent in inert cater gas.

* * * * *